United States Patent
Wildhagen et al.

(10) Patent No.: US 12,290,349 B2
(45) Date of Patent: May 6, 2025

(54) METHOD FOR CHECKING A POSITION AND/OR AN ORIENTATION OF A CATHETER TIP OF A CATHETER

(71) Applicant: B. Braun Melsungen AG, Melsungen (DE)

(72) Inventors: Jens Wildhagen, Hannover (DE); David Thalmann, Kaufungen (DE); Dejana Vukovic, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 57 days.

(21) Appl. No.: 18/274,358

(22) PCT Filed: Feb. 21, 2022

(86) PCT No.: PCT/EP2022/054220
§ 371 (c)(1),
(2) Date: Jul. 26, 2023

(87) PCT Pub. No.: WO2022/179976
PCT Pub. Date: Sep. 1, 2022

(65) Prior Publication Data
US 2024/0081673 A1 Mar. 14, 2024

(30) Foreign Application Priority Data
Feb. 23, 2021 (DE) .................... 10 2021 201 700.2

(51) Int. Cl.
*A61B 5/06* (2006.01)
*A61B 5/00* (2006.01)

(52) U.S. Cl.
CPC ............ *A61B 5/068* (2013.01); *A61B 5/6852* (2013.01)

(58) Field of Classification Search
CPC ........ A61B 5/065; A61B 5/068; A61B 5/6852
See application file for complete search history.

(56) References Cited

U.S. PATENT DOCUMENTS

| | | | |
|---|---|---|---|
| 2008/0097232 A1* | 4/2008 | Rothenberg | A61B 5/349 600/509 |
| 2009/0318995 A1* | 12/2009 | Keel | A61N 1/36843 607/17 |
| 2018/0132877 A1 | 5/2018 | Friedman et al. | |
| 2019/0038897 A1 | 2/2019 | Thakkar et al. | |
| 2020/0268953 A1 | 8/2020 | Ferrari et al. | |

FOREIGN PATENT DOCUMENTS

DE   112012003687 T5   7/2014

OTHER PUBLICATIONS

Schummer et al., "Modified ECG-guidance for optimal central venous catheter tip positioning. A transesophageal echocardiography controlled study," Randomized Controlled Trial, Anesthetist, Oct. 2005, 54 (10), 9 pages.

Search Report received in International Application No. PCT/EP2022/054220 dated May 27, 2022, with translation, 8 pages.

\* cited by examiner

*Primary Examiner* — Katherine L Fernandez
(74) *Attorney, Agent, or Firm* — Christopher A. Rothe; CM Law

(57) ABSTRACT

A method for checking a position and/or an orientation of a catheter tip of a catheter, in particular a central venous catheter, in a patient's body, a medical system set up for carrying out such a method, and a use of such a method during a catheterization.

8 Claims, 10 Drawing Sheets

METHOD FOR CHECKING A POSITION AND/OR AN ORIENTATION OF A CATHETER TIP OF A CATHETER

CROSS-REFERENCE TO RELATED APPLICATIONS

This application is the United States national stage entry of International Application No. PCT/EP2022/054220, filed on Feb. 21, 2022, and claims priority to German Application No. 10 2021 201 700.2, filed on Feb. 23, 2021. The contents of International Application No. PCT/EP2022/054220 and German Application No. 10 2021 201 700.2 are incorporated by reference herein in their entireties.

FIELD

The invention relates to a method for checking a position and/or an orientation of a catheter tip of a catheter, in particular a central venous catheter, in a patient's body. The invention also relates to a medical system configured to carry out such a method.

BACKGROUND

Catheters, in particular central venous catheters, are generally known in medicine. When applying a catheter, its catheter tip is inserted into an access site on the body and advanced to a desired location.

Central venous catheters are usually inserted into the venous system through a vein in the upper half of the body. The catheter tip is usually advanced into the area of the right atrium. Insufficiently precise positioning of the catheter tip can lead to problems. To avoid such problems, it is necessary to check the position of the catheter tip. Various methods are known for this in clinical practice.

In one known method, the position of the catheter tip is detected radiologically after or already during application. The associated exposure to radiation for the patient stands in the way of a broad application of the method. In addition, the method is comparatively time-consuming and costly.

In another known method, the position is checked electrocardiographically (e.g. W. Schummer et al.: "Optimierte Positionierung zentraler Venenkatheter durch eine modifizierte Anwendung der intravasalen Elektrokardiographie [Optimized positioning of central venous catheters by a modified application of intravascular electrocardiography]", Anasthesist 54 (2005), pages 983-990). An ECG signal is derived between a skin electrode attached to the patient's body surface and a Seldinger wire of the catheter. The known method makes use of the fact that the P wave of the ECG signal changes as a function of the advancement of the catheter tip. The P wave represents the electrical excitation of the atrium. When the catheter tip enters the atrium, there is a characteristic change in the P wave. The position is thus checked by observing the derived ECG signal. On the one hand, the known electrocardiographic method requires the skin electrode to be attached to the patient's body surface. In addition, an ECG device and monitor must be provided in order to observe the ECG signal.

SUMMARY

The object of the invention is to provide a method and a medical system of the type mentioned at the outset, each of which offers advantages over the prior art.

The method according to the invention for checking a position and/or an orientation of a catheter tip of a catheter, in particular a central venous catheter, in a patient's body has the steps of: a) detecting a first electrical potential by means of a first electrode arranged on the catheter tip and generating a first signal which represents a time curve of the detected first electrical potential; b) detecting a second electrical potential by means of a second electrode arranged on the catheter tip and spaced apart proximally from the first electrode and generating a second signal which represents a time curve of the detected second electrical potential; c) generating a differential signal as a function of the first signal and the second signal, the differential signal representing a time curve of an electrical voltage between the first electrode and the second electrode; d) checking the position and/or the orientation of the catheter tip by comparing the differential signal and a reference signal which represents a desired position and/or orientation of the catheter tip. The invention is based on the consideration that catheters, in particular central venous catheters, are often not applied in the surgical environment. In other words, the patient is often not connected to an ECG device via skin electrodes when the catheter is being applied. The application of skin electrodes is time-consuming. The provision of an ECG device solely for checking the position means additional expenditure on equipment. The solution according to the invention makes it possible in particular to dispense with the attachment of skin electrodes to the patient's body surface. On the one hand, this makes it possible to save time. This is of great advantage, especially in medical emergencies. On the other hand, the additional expenditure on equipment for providing the ECG device can be omitted. This can save costs. In contrast to the known electrocardiographic method, the invention in particular does not provide for any dissipation of signals on the patient's skin surface. Instead, preferably exclusively, catheter-side signals are conducted, namely the first signal and the second signal. For this purpose, the first and second electrodes are arranged on the catheter tip. The first and second signals represent the electrical potential at the respective electrode, with the electrical potentials resulting from the electrical activity of the heart muscle cells. In particular, the inventors have recognized: As long as the first electrode and the second electrode are in a vein, for example the superior vena cava, in front of the right atrium, both electrodes have a similar electrical potential profile. That is, the electrical voltage between the first electrode and the second electrode is small. As soon as the first electrode arranged distally on the catheter tip migrates into the atrium, the potential difference between the first electrode and the second electrode changes. The generated differential signal thus also changes. To put it simply, a characteristic time curve and/or a change in amplitude of the differential signal is/are used as a measurement signal for checking the position. Furthermore, the differential signal, i.e. the voltage between the first electrode and the second electrode, can be used to check the orientation of the catheter tip. This is because, as soon as the catheter tip, together with the first electrode and the second electrode, moves away from the heart, a polarity of the differential signal changes. The polarity of the differential signal indicates whether the catheter tip is moving toward or away from the heart. Thus, even when the catheter is being applied, it can be recognized whether the catheter tip—to put it bluntly—is turning toward the head instead of toward the heart.

The solution according to the invention is suitable in a particularly advantageous manner for central venous catheters, PICCs (Peripherally Inserted Central Venous Catheters) and so-called midlines. However, the solution according to the invention is not limited to such catheters, but is also advantageously suitable, for example, for pulmonary artery catheters, dialysis catheters and/or arterial catheters.

In one embodiment, the method has the step of: outputting the differential signal and/or a check signal which represents a deviation between the differential signal and the reference signal. In other words, the check signal represents a deviation between the actual position and/or orientation and the desired position and/or orientation. The differential signal and/or the check signal is/are preferably output in a way that is optically and/or acoustically perceptible to medical personnel. This is particularly user-friendly and allows the position and/or orientation to be checked easily and reliably.

In a further embodiment, checking the orientation of the catheter tip comprises the step of detecting and evaluating a change in sign of the differential signal, the change in sign representing a change in a polarity of the first electrode and the second electrode. The inventors have recognized that the polarity of the first electrode and/or the second electrode allows to draw conclusions about the orientation of the catheter tip in relation to the heart. In other words, the polarity of the electrical voltage between the first electrode and the second electrode indicates whether the catheter tip is oriented toward or away from the heart. The associated change in sign of the differential signal can be detected and evaluated using simple means. The orientation of the catheter tip can be checked by this embodiment with comparatively little outlay on equipment.

In a further embodiment, the first signal is conducted from the catheter tip by means of a first conductor wire and/or the second signal is conducted from the catheter tip by means of a second conductor wire. Such wired dissipation of the signals is possible with technically simple means. The first conductor wire and/or the second conductor wire extend(s) from the respective electrode in the direction of a proximal end of the catheter. Preferably, the first conductor wire and/or the second conductor wire is/are elongated inside the catheter. At their proximal ends facing away from the catheter tip, the first conductor wire and/or the second conductor wire is/are connected in a signal-transmitting manner to an evaluation device set up for signal processing. In this embodiment, the first electrode and/or the second electrode can be formed by a distal end of the respective conductor wire.

In a further embodiment, the first signal is conducted from the catheter tip via a fluid-filled first catheter lumen and/or the second signal is conducted from the catheter tip via a fluid-filled second catheter lumen. This embodiment makes it possible in particular to dispense with wired dissipation of the first signal and/or the second signal. In the actual application of the catheter, the first catheter lumen and/or the second catheter lumen is/are provided for supplying a medication fluid and/or for removing blood from the patient's venous system. As a result, the first and/or second catheter lumen has a particularly advantageous multifunction in this embodiment. This simplifies the construction of the catheter. This ultimately allows simple and inexpensive manufacturability. In this embodiment, the first electrode and/or the second electrode can be formed by a distal end opening of the respective catheter lumen. A further simplified construction of the catheter can thereby be achieved.

In a further embodiment, the method has the steps of: detecting a third electrical potential by means of a third electrode arranged on the catheter tip and spaced apart proximally from the second electrode and generating a third signal which represents a time curve of the detected third electrical potential; generating a further differential signal as a function of the second signal and the third signal, the further differential signal representing a time curve of an electrical voltage between the second electrode and the third electrode; wherein the checking of the position and/or the orientation of the catheter tip comprises a comparison of the differential signal and the further differential signal. To put it simply, in this embodiment, the electrical potential is detected at an additional point in the area of the catheter tip. The third electrode is provided for this purpose and is spaced apart proximally from the second electrode. The inventors have recognized that greater safety can be achieved in this way. The further differential signal and the differential signal are compared with one another in order to check the position and/or orientation. This comparison can be made using appropriate algorithms, for example by subtracting the further differential signal from the differential signal or vice versa. The third signal can be conducted from the catheter tip in a manner corresponding to the first and/or the second signal. For example, a third conductor wire or a fluid-filled third catheter lumen can be provided for this purpose. Accordingly, the third electrode can be formed by a distal end of the third conductor wire or by a distal end opening of the third catheter lumen. It goes without saying that in further embodiments of the invention more than just the first, second and third electrical potential can be detected at the catheter tip. Accordingly, more than the first, second and third electrode can be arranged on the catheter tip. For example, the arrangement of four, five, six, more than six or more than ten electrodes is conceivable.

The invention also relates to a medical system for carrying out a method according to the preceding description, having a catheter, in particular a central venous catheter, with a catheter tip on which at least a first electrode and a second electrode are arranged, the second electrode being spaced apart from the first electrode in the proximal direction, wherein the first electrode is configured to detect a first electrical potential and to generate a first signal which represents a time curve of the first electrical potential, and wherein the second electrode is configured to detect a second electrical potential and to generate a second signal which represents a time curve of the second electrical potential; and having an evaluation device which is connected to the first electrode and the second electrode, wherein the evaluation device is configured to generate a differential signal as a function of the first signal and the second signal, the differential signal representing a time curve of an electrical voltage between the first electrode and the second electrode. The medical system according to the invention makes it possible to check the position and/or orientation of the catheter tip in a time-saving and reliable manner with little equipment. Otherwise, to avoid repetition, reference is made to the disclosure of the method according to the invention. The statements made there with regard to advantages associated with the solution according to the invention apply, mutatis mutandis, to the medical system according to the invention. The catheter is designed in particular as a central venous catheter, PICC (Peripherally Inserted Central Venous Catheter), midline, pulmonary artery catheter, dialysis catheter or arterial catheter. The first electrode and the second electrode are arranged in the region of the catheter tip and are preferably each arranged and/or formed on an outer lateral surface of the catheter tip. The evaluation device is configured to evaluate the first and second signals detected and/or generated by means of the first and second electrodes. In particular, the evaluation device is configured to generate the differential signal as a function of the first and second signals. The evaluation device can be connected to the first electrode and the second electrode in a wired and/or wireless manner. For the wired connection, the catheter has at least a first conductor wire, which is assigned to the first electrode, and/or a second conductor wire, which is assigned to the second electrode. Alternatively or additionally, a wireless connection is provided via a first catheter lumen, which is assigned to the first electrode, and/or a second catheter lumen, which is assigned to the second electrode. When the catheter is actually used, the first catheter lumen and/or the second catheter lumen is/are filled with (electrically conductive) fluid. This enables wireless signal dissipation.

In a further embodiment, the evaluation device is configured to compare the differential signal with a reference signal which represents a desired position and/or orientation of the catheter tip. In other words, the evaluation device is configured to evaluate a curve profile of the differential signal. A significant change in the curve profile allows a conclusion to be drawn about the position and/or orientation of the catheter tip.

In a further embodiment, provision is made of an output device which is connected to the evaluation device and is configured to output the differential signal and/or a check signal which represents a deviation between the differential signal and the reference signal. The output device can be set up for optical and/or acoustic output of the relevant signal. The output device is preferably integrated into the evaluation device or vice versa. The output device can have a display, a screen, a projection device or the like.

In a further embodiment, at least one further, third electrode is arranged on the catheter tip and is spaced apart from the second electrode in the proximal direction, wherein the third electrode is configured to detect a third electrical potential and to generate a third signal which represents a time curve of the detected third electrical potential, wherein the evaluation device is connected to the third electrode and is configured to generate a further differential signal as a function of the second signal and the third signal, the further differential signal representing a time curve of an electrical voltage between the second electrode and the third electrode, and wherein the evaluation device is configured to compare the further differential signal and the differential signal. To avoid repetition, reference is made to the relevant description. The statements made there apply, mutatis mutandis, to this embodiment of the medical system according to the invention.

BRIEF DESCRIPTION OF THE DRAWINGS

Further advantages and features of the invention emerge from the following description of preferred exemplary embodiments of the invention which are illustrated with the aid of the drawings.

DETAILED DESCRIPTION

Figure 2:
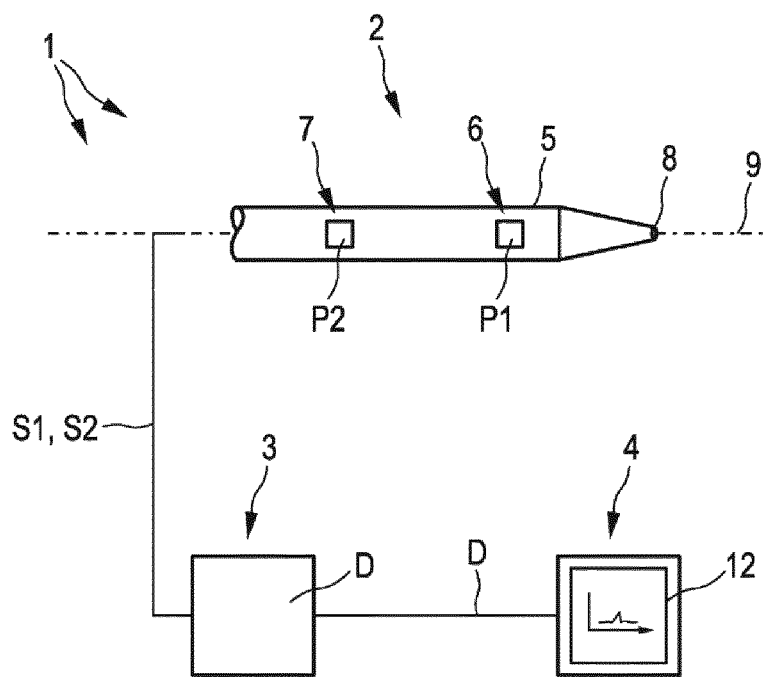
FIG. 2 shows a schematic view of one embodiment of a medical system according to the invention which is configured to carry out an embodiment of the method according to the invention and has a catheter, an evaluation device and an output device.

According to FIG. 2, a medical system 1 having a catheter 2, an evaluation device 3 and an output device 4 is provided. In FIG. 2, the medical system 1 is shown in a schematically highly simplified manner.

The catheter 2 is only shown in the area of its catheter tip 5. The catheter tip 5 is arranged at a distal end of the catheter 2. In the illustrated embodiment, the catheter 2 is a central venous catheter.

In embodiments that are not shown in the drawing, the catheter can instead be a PICC catheter, a midline, a pulmonary artery catheter, a dialysis catheter or an arterial catheter.

The catheter 2 has a first electrode 6 and a second electrode 7 in the region of its catheter tip 5. The first electrode 6 is arranged comparatively closer to a distal end 8 of the catheter tip 5 than the second electrode 7. In other words, the second electrode 7 is arranged on the catheter tip 5 in a manner spaced apart from the first electrode 6 in the proximal direction. The second electrode 7 is spaced apart from the first electrode 6 along a longitudinal axis 9 extending between the distal end 8 and a proximal end (not shown). The first and second electrodes 6, 7 are each configured to detect an electrical potential. The electrical potential that can be detected or that has been detected at the first electrode 6 can also be referred to as the first electrical potential P1. The electrical potential assigned to the second electrode 7 can accordingly be referred to as the second electrical potential P2.

In the embodiment shown, the first and second electrodes 6, 7 are each configured to generate a signal which represents a time curve of the electrical potential detected in each case. In this respect, the first electrode 6 is configured to generate a first signal S1. The second electrode 7 is configured to generate a second signal S2. The first signal S1 represents the time curve of the first electrical potential P1 detected by means of the first electrode 6. Accordingly, the second signal S2 represents the time curve of the second electrical potential P2 detected by means of the second electrode 7.

Alternatively or additionally, the evaluation device 3 can be configured to generate the first and second signals S1, S2 as a function of the first and second electrical potentials P1, P2 detected by means of the first and second electrodes 6, 7.

The first and second electrodes 6, 7 are each connected to the evaluation device 3. This connection serves to transmit the electrical potentials P1, P2 detected by means of the electrodes 6, 7 and/or the signals S1, S2, provided the latter are generated by means of the electrodes 6, 7. This transmission can also be referred to as lead or catheter lead according to a common terminology used in medicine.

Figure 3:
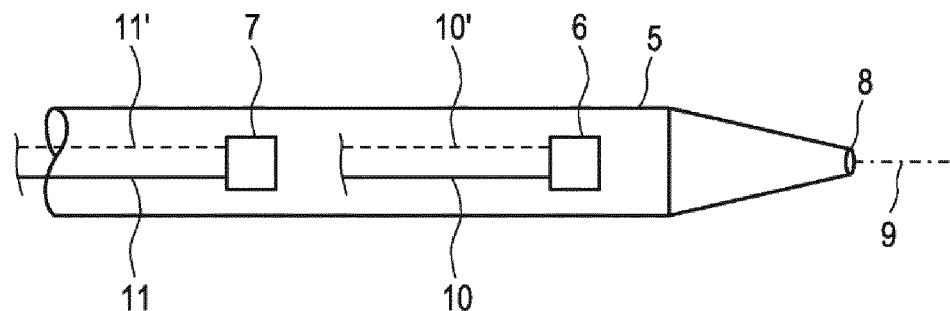
FIG. 3 shows a schematic detailed view of the catheter tip of the catheter according to FIG. 2, with a first and second electrode being arranged on the catheter tip.

As shown with FIG. 3, the lead can be wired or wireless. In this case, FIG. 3 illustrates both variants, with either wired or wireless leads preferably being provided.

A first conductor wire 10 and a second conductor wire 11 are provided for the wired lead. The first conductor wire 10 is assigned to the first electrode 6. The second conductor wire 11 is assigned to the second electrode 7. The conductor wires 10, 11 produce an electrically conductive connection between the electrodes 6, 7 on the one hand and the evaluation device 3 on the other hand. The conductor wires 10, 11 are preferably elongated inside the catheter 2. The arrangement shown with FIG. 3 is to be regarded as purely exemplary and schematically highly simplified.

The electrodes 6, 7 can be manufactured as separate components and/or sections and then electrically conductively connected to the respective conductor wire 10, 11. Alternatively, the electrodes 6, 7 can be formed by a distal end of the respective conductor wire 10, 11.

For said wireless lead, the catheter 2 can have a first catheter lumen 10' assigned to the first electrode 6. Accordingly, a second catheter lumen 11' can be assigned to the second electrode 7. During use of the catheter 2, the catheter lumens 10', 11' are provided for fluid conduction in a way that is fundamentally known to a person skilled in the art. For example, a medical fluid can be administered or blood can be taken by means of the catheter lumens 10', 11'. In the present case, the catheter lumens 10', 11' are also used for said lead, which takes place via the electrically conductive fluid located in the catheter lumens 10', 11' during use of the catheter 2. The catheter lumens 10', 11' are illustrated in a highly simplified manner with dashed lines with FIG. 3. The first electrode 6 can be formed by a distal end opening of the first catheter lumen 10'. The second electrode 7 can be formed by a distal end opening of the second catheter lumen 11'.

The evaluation device 3 is configured to evaluate the signals S1, S2 detected or generated by means of the electrodes 6, 7. In the embodiment shown, the signal evaluation includes the generation of a differential signal D. The differential signal D is generated as a function of the first signal S1 and the second signal S2 and represents an electrical voltage prevailing between the first electrode 6 and the second electrode 7 (potential difference between the first electrical potential P1 and the second electrical potential P2).

In the embodiment shown, the evaluation device 3 is connected to the output device 4. In the present case, the output device 4 is set up for the optical output of the differential signal D. In the present case, the output device 4 has a monitor 12 for this purpose. An exemplary time curve of the differential signal D is shown schematically by means of the monitor 12 with reference to FIG. 2.

Figure 4:
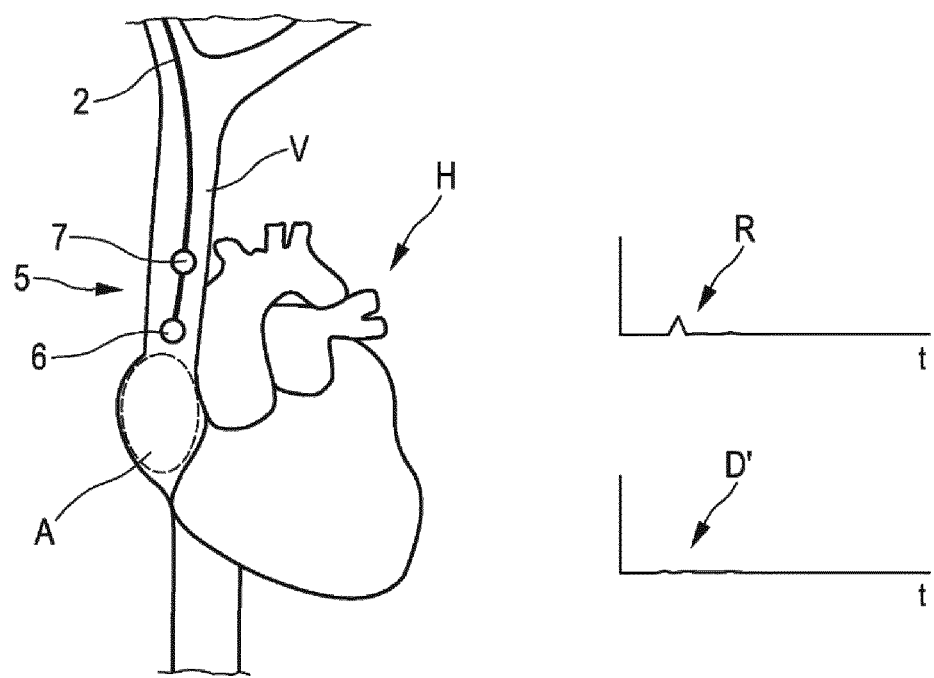
FIGS. 4 to 6 show different application situations when applying the catheter according to FIG. 2 to illustrate the method according to FIG. 1.
Figure 5:
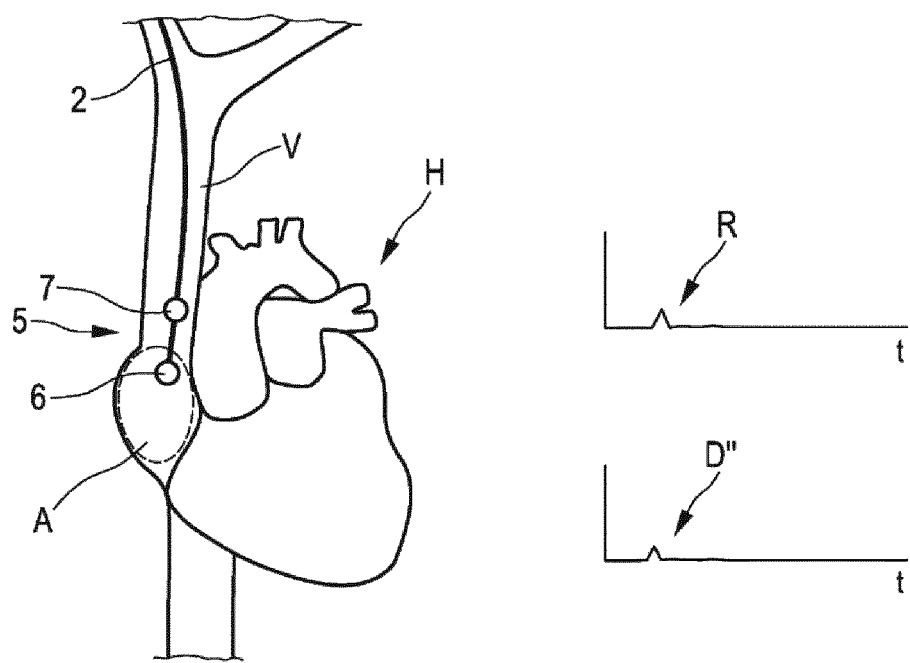
Figure 6:
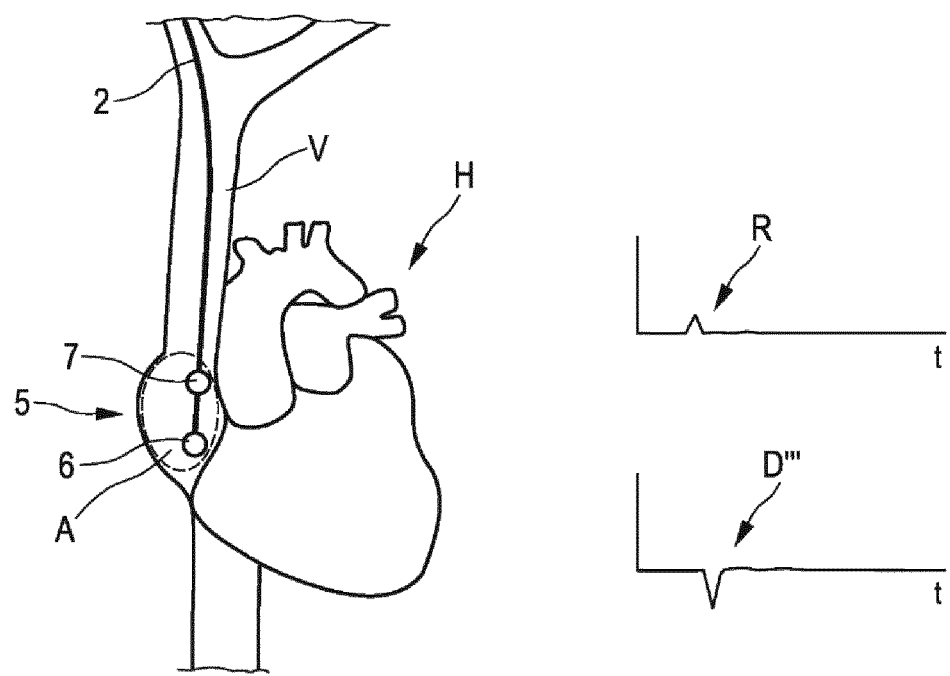

The catheter 2 is applied in a manner that is fundamentally known to a person skilled in the art. In this case, the catheter 2 is usually introduced into the venous system of a patient via a vein in the upper half of the body. The catheter tip 5 is advanced into the area of the right atrium of the heart H (FIGS. 4 to 6). The right atrium is hereinafter referred to as atrium A. It is known that insufficiently precise positioning of the catheter tip 5 in relation to the atrium A is problematic. In order to avoid such problems, it is therefore necessary to check the position of the catheter tip 5. The medical system 1 allows such a check. For a more detailed explanation, reference is made in particular to FIGS. 4 to 6 below.

FIGS. 4 to 6 show examples of different situations when applying the catheter 2.

FIG. 4 shows a first situation in which the catheter tip 5 has been advanced in a fundamentally known manner via the superior vena cava V to just before the atrium A. The position of the catheter tip 5 shown with FIG. 4 can also be referred to as the first position. Both the first electrode 6 and the second electrode 7 are arranged outside the atrium A in this position.

FIG. 5 shows a second situation in which the catheter tip 5 has been advanced further in the direction of the atrium A, starting from the first position. The position of the catheter tip 5 shown with FIG. 5 can also be referred to as the second position. In this position, the first electrode 6 is located within the atrium A. In contrast, the second electrode 7 is arranged outside of the atrium A in the superior vena cava V.

A third situation is shown as an example with reference to FIG. 6. In this situation, the catheter tip 5 has been advanced further, starting from the second position. The position of the catheter tip 5 shown in FIG. 6 can also be referred to as the third position. In the third position, the first electrode 6 and the second electrode 7 are within the atrium A.

During the application of the catheter and the associated advance movement of the catheter tip 5, the electrical potentials P1, P2 and thus the electrical voltage, represented by the differential signal D, between the electrodes 6, 7 are detected, preferably continuously.

The inventors have recognized that the electrical voltage—and thus the differential signal D—changes as a function of the position of the catheter tip 5 in relation to the atrium A. Put simply, the position of the catheter tip 5 can be checked on the basis of the detected electrical voltage and thus the differential signal D.

As long as the first electrode 6 and the second electrode 7 are in the vena cava V in front of the atrium A, a similar electrical potential is present at the two electrodes 6, 7. In other words, the electrical voltage is comparatively small in the first position (FIG. 4). This is illustrated by the exemplary time curve, shown in FIG. 4, of a differential signal D' that results in the first situation. The time curve of the differential signal D' shows no significant swing.

As soon as the first electrode 6 enters the atrium A (FIG. 5), there is a change in the electrical potentials detected by means of the electrodes 6, 7 and, as a result, in the voltage present between the electrodes 6, 7. The time curve of the differential signal changes accordingly. This is illustrated in FIG. 5 by a differential signal D". Compared to the differential signal D' in the first position (FIG. 4), the differential signal D" has a changed signal profile over time.

In the third position (FIG. 6), there is another change in the voltage between the first electrode 6 and the second electrode 7. The time curve of the differential signal changes accordingly, which is shown by way of example with FIG. 4 by the differential signal D'''.

The characteristic change in the time curve of the differential signal D, symbolized by the exemplary curve profiles D', D" and D''', allows a conclusion to be drawn about the position of the catheter tip 5 in relation to the atrium A. This allows the position of the catheter tip 5 to be checked.

In the embodiment shown, the check comprises comparing the differential signal D with a reference signal R. The reference signal R represents a desired position and/or a desired orientation of the catheter tip 5.

The differential signal D and the reference signal R can be compared visually, for example, by medical personnel using the screen 12. Alternatively or additionally, the comparison can take place using the evaluation device 3.

Figure 1:
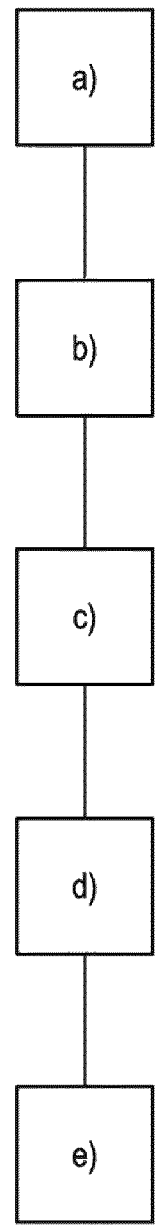
FIG. 1 shows, in a schematic diagram representation, individual steps of one embodiment of a method according to the invention.

The underlying method is illustrated in a schematically simplified manner with reference to FIG. 1 and comprises steps a) to e). Briefly in detail:

According to step a), the first signal S1 is generated on the basis of the first electrical potential P1 detected by means of the first electrode 6.

According to step b), the second signal S2 is generated accordingly. This is based on the second electrical potential P2 detected by means of the second electrode 7.

According to step c), the differential signal D is generated. In the present case, this is done by means of the evaluation device 3.

According to step d), the position of the catheter tip 5 is checked. In the present case, this is done by means of said comparison between the (time curve) of the differential signal D and the reference signal R. The comparison can be carried out by means of a visual check on the screen 12. Alternatively or additionally, the differential signal D and the reference signal R are compared with one another by means of the evaluation device 3, preferably by means of algorithms suitable for this purpose. In the simplest case, the comparison involves a simple subtraction.

If a visual comparison is provided, the differential signal D is output according to step e). Alternatively or additionally, a check signal that represents the deviation between the differential signal D and the reference signal R can be output.

Figure 7:
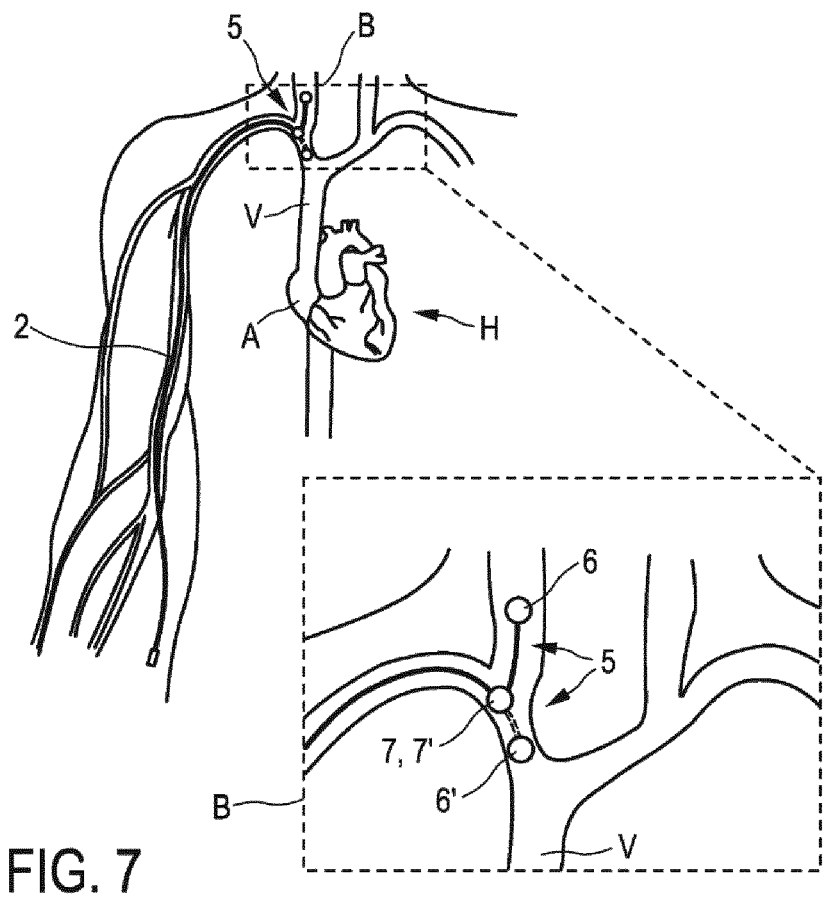
FIG. 7 shows a further application situation to illustrate the method, with two different positions and/or orientations of the catheter tip being shown in a superimposed form.
Figure 8:
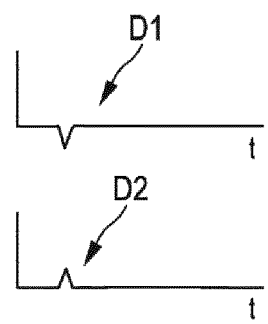
FIG. 8 shows schematic representations of different signal curves which are assigned to the application situation shown with reference to FIG. 7 and represent the different orientations of the catheter tip shown there.

In addition to checking the position, the medical system 1 also allows the orientation of the catheter tip 5 to be checked as an alternative or in addition. This is shown in FIGS. 7 and 8. FIG. 7 shows two graphically superimposed situations during the application of the catheter 2. In the embodiment shown in FIG. 7, the catheter is designed as a PICC catheter and accordingly fed into the venous system starting from the crook of the arm. In both situations shown, the catheter tip 5 is arranged in a region B above the superior vena cava V.

In the first situation shown, the catheter tip 5 is unintentionally not advanced in the direction of the atrium A, but instead in the direction of the head. This situation is assigned the reference signs 6 and 7 of the first and second electrodes. In the second situation, the catheter tip 5 is instead advanced in the direction of the atrium A as required. The apostrophized reference signs 6' and 7' are assigned to this second situation in the region B shown in enlarged form.

The inventors have recognized that the polarity of the differential signal changes depending on the orientation of the catheter tip 5 in relation to the heart H. This is shown in FIG. 8. Two exemplary signal profiles D1, D2 of the differential signal D are shown there. The signal profile D1 is assigned to the first situation and thus to the orientation of the catheter tip 5 in the direction of the head. The second signal profile D2 is assigned to the orientation of the catheter tip 5 in the direction of the heart H (second situation). Depending on the orientation of the catheter tip 5, the polarity of the differential signal is different. In other words, the sign of the differential signal D changes. This is symbolized by the signal profiles D1, D2. As a result, the orientation of the catheter tip 5 can be checked in a simple manner by means of a corresponding signal evaluation.

Figure 9:
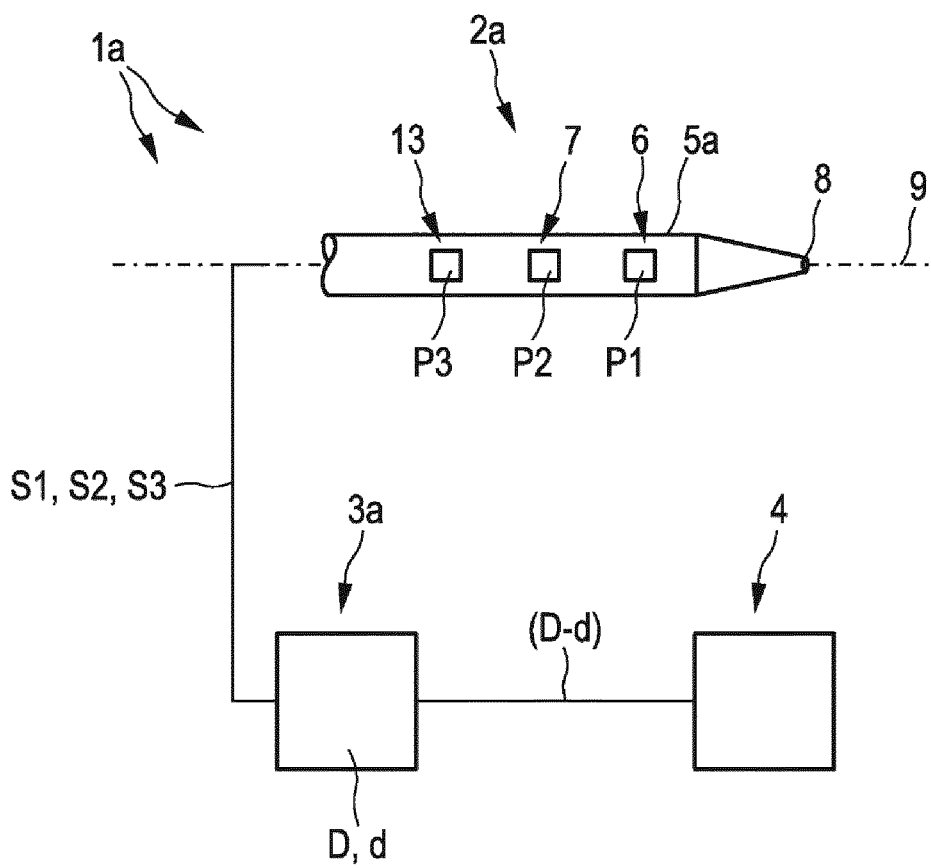
FIG. 9 shows a further embodiment of a medical system according to the invention, with an additional, third electrode being arranged on the catheter tip.

FIG. 9 shows a medical system 1a which is designed to be largely identical to the medical system 1 according to FIG. 2. The functionality is also largely identical. Only major differences between the medical system 1a and the medical system 1 according to FIG. 2 are discussed below.

The main difference is the number of electrodes at the catheter tip 5a. In the present case, a third electrode 13 is provided on the catheter 2a in addition to the first and second electrodes 5, 7. The third electrode 13 is spaced apart from the second electrode 7 in the proximal direction along the longitudinal axis 9. The third electrode 13 is configured to detect a third electrical potential P3 and to generate a third signal S3. To put it simply, the third electrode 13 is identical to the first and second electrodes 6, 7 apart from its arrangement. For the dissipation of the signal S3 and the connection provided for this purpose between the third electrode 13 and the evaluation device 3a, the statements already made regarding the dissipation of the signals S1, S2 (FIG. 3) apply accordingly.

Another difference is that the evaluation device 3a is also configured to process the third signal S3. A further differential signal d is generated as a function of the third signal S3 and the second signal S2. The further differential signal d represents a time curve of an electrical voltage between the second electrode 7 and the third electrode 13.

In the embodiment according to FIG. 9, checking the position and/or the orientation of the catheter tip 5 involves comparing the differential signal D and the further differential signal d. In the simplest case, the further differential signal d is subtracted from the differential signal D. A comparison signal D-d resulting from the comparison can, for example, be output by means of the output device 4 and used as a basis for the check.

Figure 10:
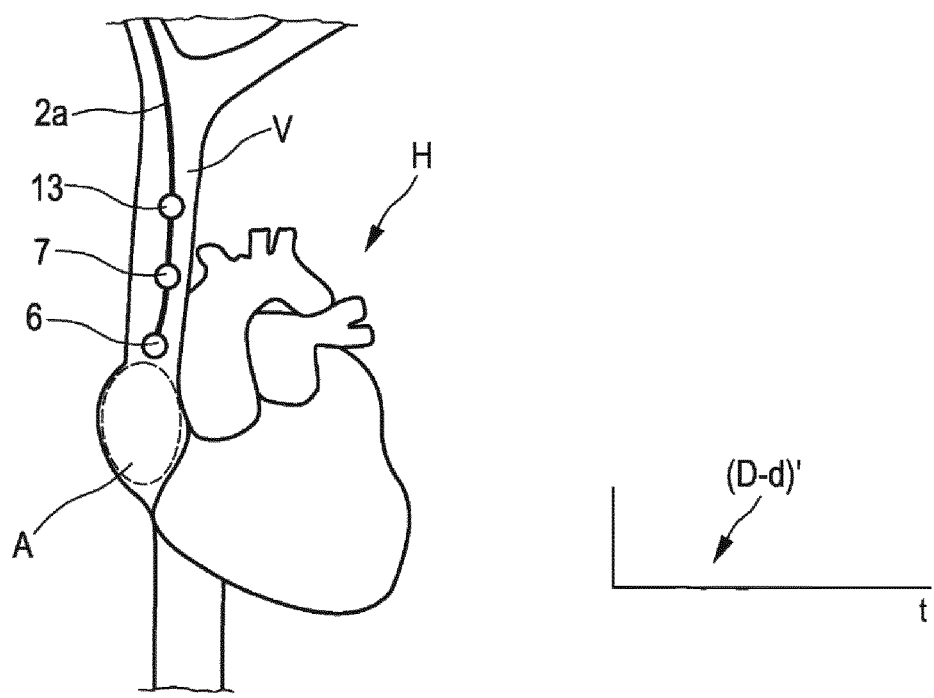
FIGS. 10 to 12 show different application situations when applying the catheter of the medical system according to FIG. 9 in a representation corresponding to FIGS. 4 to 6.
Figure 11:
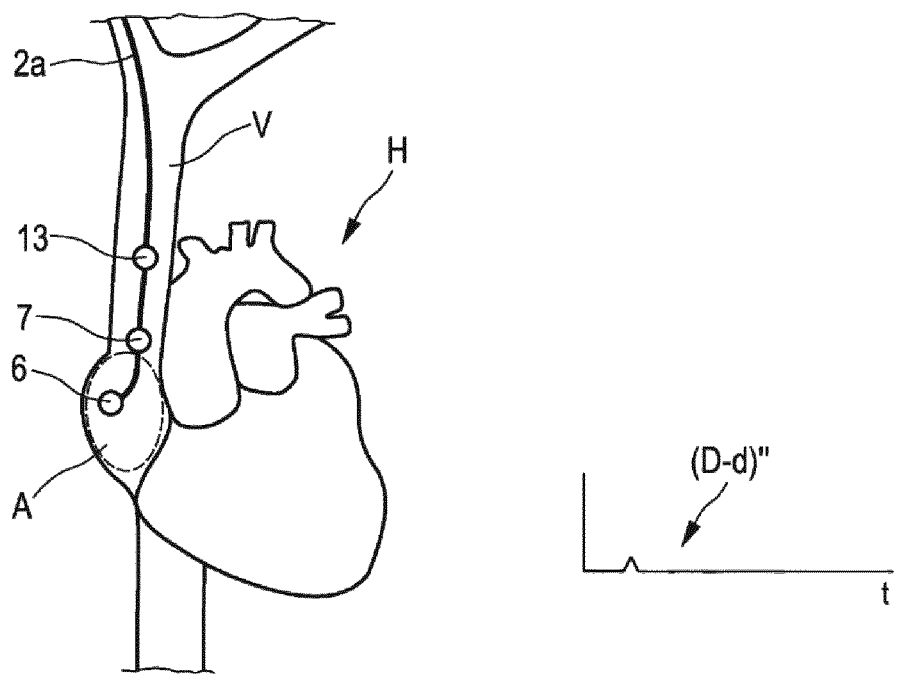
Figure 12:
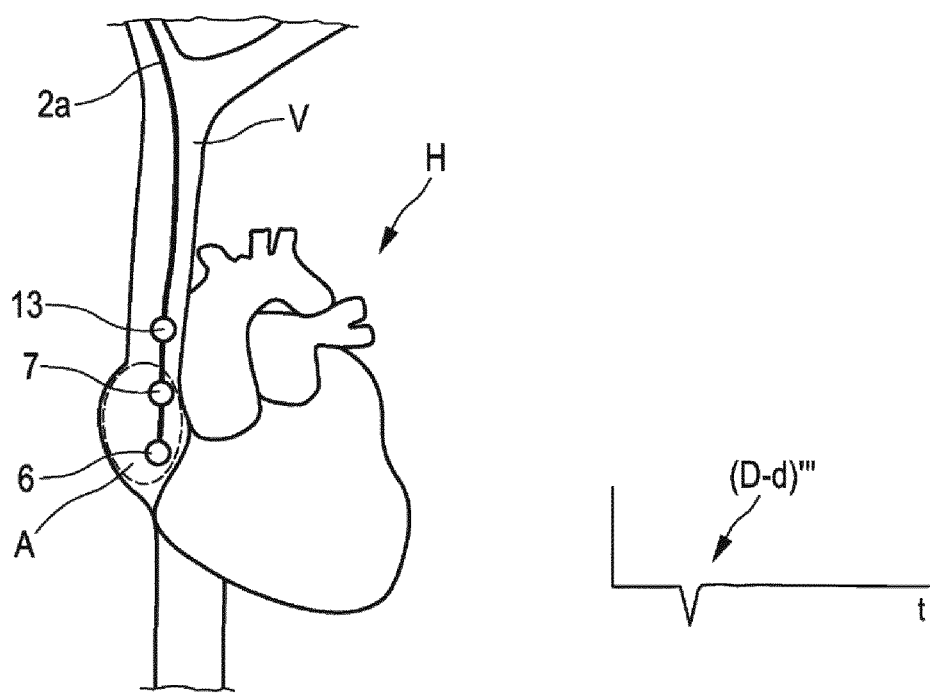

FIGS. 10 to 12, corresponding to FIGS. 4 to 6, show different situations when applying the catheter 2a. The signal profiles shown there symbolize different characteristic signal profiles (D-d)', (D-d)", (D-d)''' of the comparison signal described above.

In the first position (FIG. 10) of the catheter tip 5a (FIG. 9), the first, second and third electrodes 6, 7, 13 are arranged outside the atrium A in the superior vena cava V. In the second position (FIG. 11), the catheter tip 5a is advanced further in the direction of the atrium A. The first electrode 6 is inside and the second and third electrodes 7, 13 are outside the atrium A. In the third position (FIG. 12), the catheter tip 5a is advanced further, with only the third electrode 13 still being arranged outside the atrium A. The resulting different voltages between the electrodes 6, 7, 13 result in the different signal profiles shown as examples. In accordance with the method explained with reference to FIGS. 4 to 6, these can be used as a basis for checking the position of the catheter tip. The inventors have recognized that the additional, third electrode 13 makes it possible to achieve greater reliability in signal detection. This may make it possible to check the position in a more reliable and/or more accurate manner. The same applies with regard to checking the orientation.

The invention claimed is:

1. A method for checking a position and an orientation of a catheter tip of a catheter in a patient's body, the method comprising:
  inserting the catheter tip into an access site in the patient's body; and
  moving the catheter tip within a vein towards a heart of the patient while:
   a) detecting a first electrical potential with a first electrode arranged on the catheter tip and generating a first signal that represents a time curve of the first electrical potential;
   b) detecting a second electrical potential with a second electrode arranged on the catheter tip and spaced apart proximally from the first electrode and generating a second signal that represents a time curve of the second electrical potential;

c) generating a differential signal as a function of the first signal and the second signal, the differential signal representing a time curve of an electrical voltage between the first electrode and the second electrode;

d) checking the position and the orientation of the catheter tip by comparing the differential signal and a reference signal that represents a desired position and orientation of the catheter tip; wherein checking the orientation of the catheter tip comprises detecting and evaluating a change in sign of the differential signal, the change in sign representing a change in a polarity of the first electrode and the second electrode.

2. The method according to claim 1, further comprising, while moving the catheter tip within the vein towards the heart of the patient outputting the differential signal and/or a check signal that represents a deviation between the differential signal and the reference signal.

3. The method according to claim 1, wherein the first signal is conducted from the catheter tip with a first conductor wire, and/or the second signal is conducted from the catheter tip with a second conductor wire.

4. The method according to claim 1, wherein the first signal is conducted from the catheter tip via a fluid-filled first catheter lumen and/or the second signal is conducted from the catheter tip via a fluid-filled second catheter lumen.

5. The method according to claim 1, further comprising, while moving the catheter tip within the vein towards the heart of the patient:

detecting a third electrical potential with a third electrode arranged on the catheter tip and spaced apart proximally from the second electrode and generating a third signal that represents a time curve of the third electrical potential; and generating a further differential signal as a function of the second signal and the third signal, the further differential signal representing a time curve of an electrical voltage between the second electrode and the third electrode, wherein checking the position and the orientation of the catheter tip comprises a comparison of the differential signal and the further differential signal.

6. A medical system for carrying out the method according to claim 1, the medical system comprising:

the catheter;

at least the first electrode and the second electrode arranged on the catheter tip; and an evaluation device, wherein the second electrode is spaced apart from the first electrode in a proximal direction, wherein the first electrode is configured to detect the first electrical potential and to generate the first signal, wherein the second electrode is configured to detect the second electrical potential and to generate the second signal, wherein the evaluation device is connected to the first electrode and the second electrode, and wherein the evaluation device is configured to generate the differential signal as a function of the first signal and the second signal and perform the checking of the position and the orientation of the catheter tip by comparing the differential signal and the reference signal, wherein checking the orientation of the catheter tip comprises the detection and the evaluation of the change in the sign of the differential signal.

7. The medical system according to claim 6, further comprising an output device connected to the evaluation device, the output device configured to output the differential signal and/or a check signal that represents a deviation between the differential signal and the reference signal.

8. The medical system according to claim 6, further comprising a third electrode arranged on the catheter tip and spaced apart from the second electrode in the proximal direction, wherein the third electrode is configured to detect a third electrical potential and to generate a third signal that represents a time curve of the third electrical potential, wherein the evaluation device is connected to the third electrode and is configured to generate a further differential signal as a function of the second signal and the third signal, the further differential signal representing a time curve of an electrical voltage between the second electrode and the third electrode, and wherein the evaluation device is configured to compare the further differential signal and the differential signal.

* * * * *